US00PP23579P3

(12) United States Plant Patent
Meilland

(10) Patent No.: US PP23,579 P3
(45) Date of Patent: May 7, 2013

(54) GROUNDCOVER ROSE NAMED 'MEIPICDEVOJ'

(50) Latin Name: *Rosa hybrida*
Varietal Denomination: Meipicdevoj

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 468 days.

(21) Appl. No.: 12/923,208

(22) Filed: Sep. 9, 2010

(65) Prior Publication Data

US 2012/0066802 P1 Mar. 15, 2012

(51) Int. Cl.
*A01H 5/00* (2006.01)

(52) U.S. Cl. ..... Plt./103
(58) Field of Classification Search ..... Plt./103, Plt./117, 144
See application file for complete search history.

*Primary Examiner* — Howard Locker
(74) *Attorney, Agent, or Firm* — Buchanan Ingersoll & Rooney

(57) ABSTRACT

A new and distinct Groundcover rose plant is provided which commonly forms clusters on a tardive basis attractive white double blossoms with excellent reblooming during the summer. The growth habit is low and mounding. The plant exhibits strong vegetation and attractive very dense dark green foliage with a semi-glossy aspect. The tolerance to disease is good particularly with respect to Marsonia. The attractive dark green foliage contrasts nicely with the white blossom coloration. The new variety is well suited for growing as attractive ornamentation in the landscape.

1 Drawing Sheet

Figures 1, 2, 3, 4, 5, 6, 7, 8, 9, 10, 11, 12, 13, 14, 15, 16, 17:
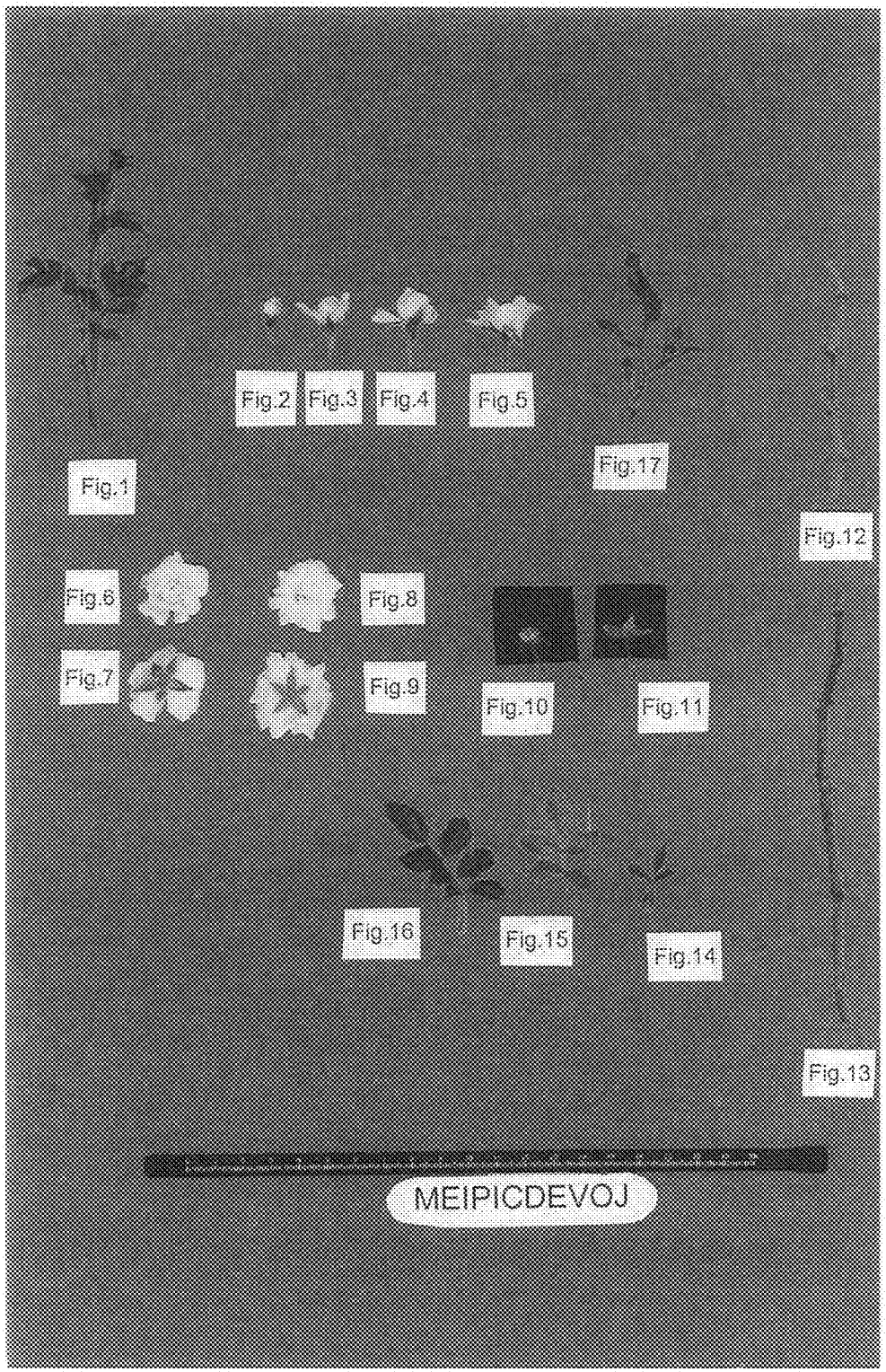

Botanical/commercial classification: *Rosa hybrida*/ Groundcover Rose Plant.

Varietal denomination: cv. Meipicdevoj.

SUMMARY OF THE INVENTION

The new variety of *Rosa hybrida* Groundcover rose plant was created by artificial pollination wherein two parents were crossed which previously had been studied in the hope that they would contribute the desired characteristics. The female parent (i.e., the seed parent) was the 'Ausblush' variety (non-patented in the United States). The male parent (i.e., the pollen parent) was the product of the cross of 'The Fairy' variety (non-patented in the United States) and the 'Korbin' variety (non-patented in the United States). The parentage of the new variety can be summarized as follows:

'Ausblush'×('The Fairy'×'Korbin').

The seeds resulting from the above pollination were sown and small plants were obtained which were physically and biologically different from each other. Selective study resulted in the identification of a single plant of the new variety.

It was found that the new Groundcover rose plant of the present invention:

(a) exhibits a low and mounding growth habit,
(b) commonly forms in clusters on a tardive basis attractive small white double blossoms with excellent reblooming during the summer,
(c) forms attractive very dense dark green semi-glossy foliage that contrasts nicely with the white blossom coloration,
(d) displays good tolerance to Marsonia, and
(e) is well suited for growing as attractive ornamentation in the landscape.

During the summer the blooming is very abundant and substantially continuous. A very dense and strong spreading growth habit is displayed. The pure white double blossoms commonly are borne in large clusters.

The new variety well meets the needs of the horticultural industry and can be grown to advantage in the landscape where attractive ornamentation is desired.

The new variety can be readily distinguished from its ancestors. For instance, the new variety readily can be distinguished from the 'Ausblush' and 'the Fairy' varieties through an inspection of the blossom coloration. Each of these ancestral varieties forms light pink blossoms unlike the white blossoms of the new variety. The new variety readily can be distinguished from the 'Korbin' variety through an inspection of the growth habit. The 'Korbin' variety displays a dissimilar upright and bushy growth habit unlike the spreading growth habit of the new variety. Also, the blossoms of the 'Korbin' variety display an intense fragrance.

The new variety has been found to undergo asexual propagation at Le Cannet-Des-Maures, Le Luc, France by a number of routes, including budding, grafting, and the use of cuttings. Such asexual propagation by the above-mentioned techniques has shown that the characteristics of the new variety are stable and are strictly transmissible by such asexual propagation from one generation to another. Accordingly, the new variety undergoes asexual propagation in a true-to-type manner.

The new variety has been named 'Meipicdevoj', and will be marketed under the ICY DRIFT trademark.

BRIEF DESCRIPTION OF THE PHOTOGRAPH

The accompanying photograph shows as nearly true as it is reasonably possible to make the same, in a color illustration of this character, typical specimens of the plant parts of the new variety. The plants had been asexually reproduced by the rooting of cuttings. The rose plants of the new variety were approximately one year of age and were observed during August growing outdoors at Le Cannet-des-Maures, Var, France. Dimensions in centimeters are indicated at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud with further opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—under surface;

FIG. 16—illustrates a specimen of a leaf with seven leaflets—plan view—upper surface; and FIG. 17—illustrates a specimen of a cluster of buds.

DETAILED DESCRIPTION

The chart used in the identification of the colors is that of The Royal Horticultural Society (R.H.S. Colour Chart), London, England. Common color terms are to be accorded their customary dictionary significance. The plants had been asexually reproduced by the rooting of cuttings. The description is based on the observation of two-year-old plants during October while growing outdoors at Le Cannet-des-Maures, Var, France.

Class: Groundcover.

Plant:

*Growth habit.*—Low mounding, and well suited for use as a ground cover.

*Blooming habit.*—During the summer very abundant and substantially continuous.

*Height.*—Commonly 30 to 45 cm.

*Width.*—Commonly 60 to 90 cm.

Branches:

*Color.*—Young stems: commonly near Yellow-Green Group 147C. Adult wood: commonly near Yellow-Green Group 147C.

*Thorns.*—On young stems: Configuration: elongated and curved downwards on the upper surface and concave on the under surface with an ovate base. Quantity: commonly approximately 9 on average over a stem length of 8 cm. Size: approximately 0.4 cm in length on average. Color: near Red Group 47D. On adult stems: Configuration: elongated and curved downwards on the upper surface and concave on the under surface with an ovate base. Quantity: commonly approximately 5 on average over a stem length of 5 cm. Size: approximately 0.4 cm in length on average. Color: near Orange Group 27A.

Leaves:

*Overall appearance.*—Very dense, attractive dark green.

*Stipules.*—Adnate, pectinate, and rather broad, approximately 1.2 cm in length on average, approximately 0.4 cm in width on average, near Green Group 138C on the upper surface, and near Green Group 138B on the under surface.

*Petioles.*—Non-glandular, approximately 1.5 cm in length on average, on the upper surface near Green Group 138B, and on the under surface near Green Group 138B with some tiny prickles.

*Rachis.*—On the upper surface near Green Group 138C, and on the under surface near Green Group 138B.

*Leaflets.*—Shape: generally oval with a rounded base and an acuminate tip. Number: 3, 5, and most often 7 or 9 per leaf. Size: the terminal leaflets commonly are approximately 2.5 cm in length on average, and approximately 1.7 cm in width at the widest point on average. Serration: slight denticulation. Texture: smooth, firm, and semi-glossy on the upper surface. Color (young foliage): on the upper surface commonly near Green Group 137B, and on the under surface commonly near Green Group 138B. Color (adult foliage): on the upper surface near Green Group 137B, and on the under surface near Green Group 138B.

Inflorescence:

*Number of flowers.*—In clusters commonly of 3 to 12 flowers per stem.

*Peduncle.*—Glandular, commonly approximately 1.7 cm in length on average, commonly approximately 1 mm in diameter on average, and near Green Group 139C in coloration.

*Sepals.*—Number: five. Size: commonly approximately 0.7 cm in length on average, and approximately 0.3 mm in width on average at the widest point. Configuration: longish and rather broad at the apex, and relatively upright at the base. Texture: smooth on the upper surface and tomentose on the under surface. Color: on the upper surface commonly near Green Group 138C, and on the under surface commonly near Green Group 139C.

*Buds.*—Shape: conical. Length: small, approximately 0.5 cm on average. Width: small, approximately 0.5 cm on average at the widest point. Color as calyx breaks: commonly near White Group 155D.

*Flower.*—Form: double and cup-shaped. Diameter: approximately 3 cm on average. Color (in course of opening): Upper surface: near White Group 155D. Under surface: near White Group 155D. Color (open flower): Upper surface: near White Group 155D. Under surface: near White Group 155D. Fragrance: none. Petal number: commonly approximately 49 to 51 on average under normal growing conditions. Petal shape: apex is acuminate and rounded and the base is wedge-shaped and rounded. Petal texture: flexible. Petal arrangement: imbricated, and without petaloids. Petal length: commonly approximately 1.2 cm on average. Petal width: commonly approximately 0.3 to 0.7 cm on average. Petal drop: good with the petals commonly detaching cleanly before drying.

Development:

*Vegetation.*—Strong.

*Blooming.*—Tardive and becomes abundant and substantially continuous during the summer.

*Tolerance to diseases.*—Very good, particularly with respect to Marsonia (*Marssonia rosae*) during observations to date.

*Hardiness.*—U.S.D.A. Hardiness Zone Nos. 5 to 10.

I claim:

1. A new and distinct Groundcover rose plant characterized by the following characteristics:

(a) exhibits a low and mounding growth habit, (b) commonly forms in clusters on a tardive basis attractive small white double blossoms with excellent reblooming during the summer, (c) forms attractive very dense dark green semi-glossy foliage that contrasts nicely with the white blossom coloration, (d) displays good tolerance to Marsonia, and (e) is well suited for growing as ornamentation in the landscape;

substantially as shown and described.

* * * * *

MEIPICDEVOJ